United States Patent [19]

Pollitzer et al.

[11] 4,009,096
[45] Feb. 22, 1977

[54] HYDROPROCESSING OF HYDROCARBONS

[75] Inventors: Ernest L. Pollitzer, Skokie; John C. Hayes, Palatine, both of Ill.

[73] Assignee: UOP Inc., Des Plaines, Ill.

[22] Filed: June 4, 1976

[21] Appl. No.: 693,059

Related U.S. Application Data

[60] Division of Ser. No. 648,544, Jan. 12, 1976, Pat. No. 3,992,464, which is a continuation-in-part of Ser. No. 522,209, Nov. 8, 1974, Pat. No. 3,960,710.

[52] U.S. Cl. .................. 208/111; 208/144; 208/255; 252/441; 252/442; 252/455 Z; 252/460; 252/466 B; 260/683 R
[51] Int. Cl.$^2$ .................. C07G 13/04; B01J 23/62
[58] Field of Search .......... 208/111, 112, 108, 109, 208/110, 144, 255; 260/683 R, 677 H

[56] References Cited

UNITED STATES PATENTS

| | | | |
|---|---|---|---|
| 2,911,357 | 11/1959 | Myers et al. | 208/138 |
| 3,576,766 | 4/1971 | Rausch | 260/683.3 |
| 3,644,198 | 2/1972 | Wilhelm | 252/460 |
| 3,751,497 | 8/1973 | Schwerdtel et al. | 260/666 A |
| 3,764,521 | 10/1973 | Mathews et al. | 208/143 |
| 3,775,300 | 11/1973 | Hayes | 208/139 |
| 3,787,514 | 1/1974 | Bernusset | 260/677 H |
| 3,788,979 | 1/1974 | Caflisch et al. | 208/255 |
| 3,804,916 | 4/1974 | Lalancette | 260/677 H |
| 3,881,696 | 5/1975 | Lepeyre et al. | 252/466 B |

*Primary Examiner*—Delbert E. Gantz
*Assistant Examiner*—G. E. Schmitkons
*Attorney, Agent, or Firm*—James R. Hoatson, Jr.; Thomas K. McBride; William H. Page II

[57] ABSTRACT

A process for hydrotreating (hydroprocessing) hydrocarbons and mixtures of hydrocarbons utilizing a catalytic composite comprising a porous carrier material containing, on an elemental basis, about 0.01 to about 2 wt.% platinum group metal, about 0.5 to about 5 wt.% cobalt, about 0.01 to about 5 wt.% tin and about 0.1 to about 3.5 wt.% halogen, wherein the platinum group metal, cobalt and tin are uniformly dispersed throughout the porous carrier material, wherein substantially all of the platinum group metal is present in the elemental metallic state, wherein substantially all of the tin is present in an oxidation state about that of the elemental metal, and wherein substantially all of the cobalt is present in the elemental metallic state or in a state which is reducible to the elemental metallic state under hydrocarbon conversion conditions, in which process there is effected a chemical consumption of hydrogen. A specific example of one such catalyst is a composite of a crystalline aluminosilicate, a platinum group metal component, a cobalt component, a tin component, and a halogen component, for utilization in a hydrocracking process. Other hydrocarbon hydroprocesses are directed toward the hydrogenation of aromatic nuclei, the ring-opening of cyclic hydrocarbons, hydrogenation, etc.

6 Claims, No Drawings

HYDROPROCESSING OF HYDROCARBONS

RELATED APPLICATIONS

The present application is a Division of our copending application, Ser. No. 648,544, filed Jan. 12, 1976 now U.S. Pat. No. 3,992,464,) which is a continuation-in-part of our copending application Ser. No. 522,209, filed Nov. 8, 1974 (now U.S. Pat. No. 3,960,710), all the teachings of which copending applications are incorporated herein by specific reference thereto.

APPLICABILITY OF INVENTION

The present invention encompasses the use of a catalytic composite of a porous carrier material, a platinum group metal component, a cobalt component, a tin component, and a halogen component, in the hydrotreating of hydrocarbons and mixtures of hydrocarbons. As utilized herein, the term "hydrotreating" is intended to be synonymous with the term "hydroprocessing", which involves the conversion of hydrocarbons at operating conditions selected to effect a chemical consumption of hydrogen. Included within the processes intended to be encompassed by the term "hydroprocessing" are hydrocracking, aromatic hydrogenation, ring-opening, hydrorefining (olefin saturation), and hydrogenation. As will be recognized, one common attribute of these processes, and the reactions being effected therein, is that they are all "hydrogen-consuming", and are, therefore, exothermic in nature.

The individual characteristics of the foregoing hydrotreating processes, including preferred operating conditions and techniques, will be hereinafter described in greater detail. The subject of the present invention is the use of a catalytic composite which has exceptional activity and resistance to deactivation when employed in a hydrogen-comsuming process. Such processes require a catalyst having both a hydrogenation function and a cracking function. More specifically, the present process uses a dual-function catalytic composite which enables substantial improvements in those hydroprocesses that have traditionally used a dual-function catalyst. The particular catalytic composite constitutes a porous carrier material, a platinum group metal component, a cobalt component, a tin component, and a halogen component; specifically, an improved hydrocracking process utilizes a crystalline aluminosilicate carrier material, a platinum group metal component, a cobalt component, a tin component and a halogen component for improved activity, product selectivity and operational stability characteristics.

Composites having dual-function catalytic activity are widely employed in many industries for the purpose of accelerating a wide spectrum of hydrocarbon conversion reactions. Generally, the cracking function is thought to be associated with an acid-acting material of the porous, adsorptive refractory inorganic oxide type which is typically utilized as the carrier material for a metallic component from the metals, or compounds of metals, of Groups V through VIII of the Periodic Table, to which the hydrogenation function is generally attributed.

Catalytic composites are used to promote a wide variety of hydrocarbon conversion reactions such as hydrocracking, isomerization, dehydrogenation, hydrogenation, desulfurization, reforming, ring-opening, cyclization, aromatization, alkylation and transalkylation, polymerization, cracking, etc., some of which reactions are hydrogen-producing while others are hydrogen-consuming. In using the term "hydrogen-consuming", we intend to exclude those processes wherein the only hydrogen consumption involves the saturation of light olefins, resulting from undesirable cracking, which produces the light paraffins, methane, ethane and propane. It is to the latter group of reactions, hydrogen-consuming, that the present invention is applicable. In many instances, the commercial application of these catalysts is in processes where more than one of these reactions proceed simultaneously. An example of this type of process is hydrocracking process wherein catalysts are utilized to effect selective hydrogenation and cracking of high molecular weight materials to produce a lower-boiling, more valuable output stream. Another such example would be the conversion of aromatic hydrocarbons into jet fuel components, principally straight, or slightly branched paraffins.

Regardless of the reaction involved, or the particular process, it is very important that the catalyst inhibit not only the capability to perform its specified functions initially, but also perform them satisfactorily for prolonged periods of time. The analytical terms employed in the art to measure how efficient a particular catalyst performs its intended functions in a particular hydrocarbon conversion process, are activity, selectivity and stability. For the purpose of discussion, these terms are conveniently defined herein for a given charge stock, as follows: 1. activity is a measure of the ability of the catalyst to convert a hydrocarbon feed stock into products at a specified severity level, where severity level alludes to the operating conditions employed — the temperature, pressure, liquid hourly space velocity and hydrogen concentration; 2. selectivity refers to the weight percent or volume percent of the reactants that are converted into the desired product and/or products; 3. stability connotes the rate of change of the activity and selectivity parameters with time — obviously, the smaller rate implying the more stable catalyst. With respect to a hydrogen-consuming process, for example hydrocracking, activity, stability and selectivity are similarly defined. Thus, "activity" connotes the quantity of charge stock, boiling above a given temperature, which is converted to hydrocarbons boiling below the given temperature. "Selectivity" refers to the quantity of converted charge stock which boils below the desired end point of the product, as well as above a minimum specified initial boiling point. "Stability" connotes the rate of change of activity and selectivity. Thus, for example, where a gas oil, boiling above about 650° F., is subjected to hydrocracking, "activity" connotes the conversion of 650° F. — plus charge stock to 650° F. — minus product. Selectivity can allude to the quantity of conversion into gasoline boiling range hydrocarbons — i.e., pentanes and heavier, normally liquid hydrocarbons boiling up to about 400° F. Stability might be conveniently expressed in terms of temperature increase required during various increments of catalyst life, in order to maintain the desired activity.

As is well known to those skilled in the art, the principal cause of observed deactivation or instability of a dual-function catalyst is associated with the fact that coke forms on the surface of the catalyst during the course of the reaction. More specifically, in the various hydrocarbon conversion processes, and especially those which are catagorized as hydrogen-consuming, the operating conditions utilized result in the formation of high molecular weight, black, solid or semi-solid, hydrogen-poor carbonaceous material which coats the surface of the catalyst and reduces its activity by shielding its active sites from the reactants. Accordingly, a major problem facing workers in this area is the development of more active and selective catalytic composites that are not as sensitive to the presence of these carbonaceous materials and/or have the capability to suppress the rate of formation of these materials at the operating conditions employed in a particular process.

We have now found a dual-function catalytic composite which possesses improved activity, selectivity and stability when employed in the hydroprocessing of hydrocarbons, wherein there is effected a chemical consumption of hydrogen. In particular, we have found that the use of a catalytic composite of a platinum group metal component, a cobalt component, a tin component and a halogen component with a porous carrier material improves the overall operation of these hydrogen-consuming processes. Moreover, we have determined that a catalytic composite of a crystalline aluminosilicate carrier material, a platinum group metal component, a cobalt component, a tin component and a halogen component, when utilized in a process for hydrocracking hydrocarbonaceous material into lower-boiling hydrocarbon products, affords substantial improvement in performance and results. As indicated, the present invention essentially involves the use of a catalyst in which a tin component, a cobalt component and a halogen component have been added to a dual-function conversion catalyst, and enables the performance characteristics of the process to be sharply and materially improved.

OBJECTS AND EMBODIMENTS

An object of the present invention is to afford a process for the hydroprocessing of a hydrocarbon, or mixture of hydrocarbons. A corollary objective is to improve the selectivity and stability of hydroprocessing utilizing a highly active, platinum group metal-containing, tin component-containing, cobalt component-containing and halogen component-containing catalytic composite.

A specific object of our invention resides in the improvement of hydrogen-consuming processes including hydrocracking, hydrorefining, ring-opening for jet fuel production, hydrogenation of aromatic hydrocarbons, etc. Therefore, in one embodiment, the present invention encompasses a hydrocarbon hydroprocess which comprises reacting a hydrocarbon with hydrogen at conditions selected to effect chemical consumption of hydrogen and in contact with a catalytic composite of a platinum group metal component, a cobalt component, a tin component, a halogen component and a porous carrier material. In another embodiment, the operating conditions include a pressure of from 400 to about 5,000 psig., an LHSV (defined as volumes of liquid hydrocarbon charger per hour per volume of catalyst disposed in the reaction zone) of from 0.1 to about 10.0, a hydrogen circulation rate of from 1,000 to about 50,000 scf./Bbl. and a maximum catalyst temperature of from 200° F. to about 900° F.

In another embodiment, our invention involves a process for hydrogenating a coke-forming hydrocarbon distillate containing di-olefinic and mono-olefinic hydrocarbons, and aromatics, which process comprises reacting said distillate with hydrogen, at a temperature below about 500° F., in contact with a catalytic composite of an alumina-containing refractory inorganic oxide, a platinum group metal component, an alkali metal component, a cobalt component, a tin component, and a halogen component and recovering an aromatic/mono-olefinic hydrocarbon concentrate substantially free from conjugated di-olefinic hydrocarbons.

Another embodiment affords a catalytic composite comprising a substantially pure crystalline aluminosilicate material, at least about 90.0% by weight of which is zeolitic, a platinum group metal component, a cobalt component, a tin component and a halogen component.

Other objects and embodiment of our invention relate to additional details regarding preferred catalytic ingredients, the concentration of components in the catalytic composite, methods of catalyst preparation, individual operating conditions for use in the various hydrotreating processes, preferred processing techniques and the like particulars which are hereinafter given in the following, more detailed summary of our invention.

SUMMARY OF THE INVENTION

As hereinabove set forth, the present invention involves the hydroprocessing of hydrocarbons and mixtures of hydrocarbons, utilizing a particular catalytic composite. The catalyst comprises a porous carrier material having combined therewith a platinum group metal component, a cobalt component, a tin component and a halogen component. The catalytic composite will also contain in some select applications, an alkali metal or alkaline-earth metal component. Considering first the porous carrier material, it is preferred that it be a porous, adsorptive, high-surface area support having a surface area of about 25 to about 500 square meters per gram. The porous carrier material is necessarily relatively refractory with respect to the operating conditions employed in the particular hydrotreating process, and it is intended to include carrier materials which have traditionally been utilized in dual-function hydrocarbon conversion catalysts. In particular, suitable carrier materials are selected from the group of amorphous refractory inorganic oxides including alumina, titania, zirconia, chromia, magnesia, thoria, boria, silica-alumina, silica-magnesia, chromia-alumina, alumina-boria, alumina-silica-boron phosphate, silica-zirconia, etc. When of the amorphous type, the preferred carrier material is a composite of alumina and silica with silica being present in an amount of about 10.0 to about 90.0% by weight.

In many hydroprocessing applications of the present invention, particularly hydrocracking heavy hydrocarbonaceous material to produce lower-boiling hydrocarbon products, the carrier material will constitute a crystalline aluminosilicate, often referred to as being zeolitic in nature. This may be naturally-occurring, or synthetically prepared, and includes mordenite, faujasite, Type A or Type U molecular sieves, etc. When utilized as the carrier material, the zeolitic material may be in the hydrogen form, or in a form which has been treated with multi-valent cations.

As hereinabove set forth, the porous carrier material, for use in the process of the present invention, is a refractory inorganic oxide, either alumina in and of itself, or in combination with one or more other refractory inorganic oxides, and particularly in combination with silica. When utilized as the sole component of the carrier material, the alumina may be of the gamma-, eta, or theta-alumina type, with gamma-, or eta-alumina giving the best results. In addition, the preferred carrier materials have an apparent bulk density of about 0.30 to about 0.70 gm./cc. and surface area characteristics such that the average pore diameter is about 20 to about 300 Angstroms, the pore volume is about 0.10 to about 1.0 milliliters per gram and the surface area is about 100 to about 500 square meters per gram. Whatever type of refractory inorganic oxide is employed, it may be activated prior to use by one or more treatments including drying, calcination, steaming, etc. For example, the alumina carrier may be prepared by adding a suitable alkaline reagent, such as ammonium hydroxide, to a salt of aluminum, such as aluminum chloride, aluminum nitrate, etc., in an amount to form an aluminum hydroxide gel which, upon drying and calcination, is converted to alumina. The carrier material may be formed in any desired shape such as spheres, pills, cakes, extrudates, powders, granules, etc., and may further be utilized in any desired size.

When a crystalline aluminosilicate, or zeolitic material, is intended for use as the carrier, it may be prepared in a number of ways. One common way is to mix solutions of sodium silicate, or collodial silica, and sodium aluminate, and allow these solutions to react to form a solid crystalline aluminosilicate. Another method is to contact a solid inorganic oxide, from the group of silica, alumina, and mixtures thereof, with an aqueous treating solution containing alkali metal cations (preferably sodium) and anions selected from the group of hydroxyl, silicate and aluminate, and allow the solid-liquid mixture to react until the desired crystalline aluminosilicate has been formed. One particular method is especially preferred when the carrier material is intended to be a crystalline aluminosilicate. This stems from the fact that the method can produce a carrier material of substantially pure crystalline aluminosilicate particles. In employing the term substantially pure, the intended connotation is an aggregate particle at least 90.0% by weight of which is zeolitic. Thus, this carrier is distinguished from an amorphous carrier material, or prior art pills and/or extrudes in which the zeolitic material might be dispersed within an amorphous matrix with the result that only about 40.0 to about 70.0% by weight of the final particle is zeolitic. The preferred method of preparing the carrier material produces crystalline aluminosilicates of the faujasite modification, and utilizes aqueous solutions of colloidal silica and sodium aluminate. Colloidal silica is a suspension in which the suspended particles are present in very finely divided form — i.e., having a particle size from about 1 to about 500 millimicrons in diameter. The type of crystalline aluminosilicate which is produced is primarily dependent upon the conditions under which crystallization occurs, with the $SiO_2/Al_2O_3$ ratio, the $Na_2O/SiO_2$ ratio, the $H_2O/Na_2O$ ratio, temperature and time being the important variables.

After the solid crystalline aluminosilicate has been formed, the mother liquid is separated from the solids by methods such as decantation or filtration. The solids are water-washed and filtered to remove undesirable ions, and to reduce the quantity of amorphous material, and are then reslurried in water to a solids concentration of about 5.0% to about 50.0%. The cake and the water are violently agitated and homogenized until the agglomerates are broken and the solids are uniformly dispersed in what appears to be a colloidal suspension. The suspension is then spray dried by conventional means such as pressuring and suspension through an orific into a hot, dry chamber. The solid particles are withdrawn from the drying chamber and are suitable for forming into finished particles of desired size and shape. The preferred form of the finshed particles is a cylindrical pill, and these may be prepared by introducing the spray-dried particles directly into a pilling machine without the addition of any extraneous lubricant or binder. The pilling machines are adjusted to produce particles having a crushing strength of from 2 to 20 pounds, and preferably from 5 to 15 pounds. The pilled faujasite carrier material, of which at least about 90.0% by weight is zeolitic, is activated catalytically by converting the sodium form either to the divalent ion form, the hydrogen form or mixtures thereof.

One essential constituent of the acidic multimetallic composite used in the present invention is a tin component, and it is an essential feature of the present invention that substantially all of the tin component in the composite is in an oxidation state above that of the elemental metal. That is, it is believed that best results are obtained when substantially all of the tin component exists in the catalytic composite in the +2 or +4 oxidation state. Accordingly, the tin component will be present in the composite as a chemical compound such as the oxide, halide, oxyhalide, and the like, wherein the tin moiety is in a positive oxidation state, or in chemical combination with the carrier material in a manner such that the tin component is in a positive oxidation state. Controlled reduction experiments with the catalytic composites produced by the preferred methods of preparing the instant catalytic composite have established that the tin component in these catalysts is in a positive oxidation state and is not reduced by contact with hydrogen at temperatures in the range of 1000° to 1200° F. It is important to note that this limitation on the oxidation state of the tin component requires extreme care in preparation and use of the present catalyst to insure that it is not subjected to a reducing atmosphere at temperatures above 1200° F. Equally significant is the observation that it is only when the tin component is in a uniformly dispersed state in the carrier material that it has the capability to maintain its positive oxidation state when subjected to hereinafter described prereduction step. Stated another way, if the tin component is not properly dispersed on the support it can be reduced in the prereduction step and result in an inferior catalyst. Based on the evidence currently available it is believed that best results are obtained when the tin component is present in the catalyst as tin oxide. The term "tin oxide" as used herein refers to a coordinated tin-oxygen complex which is not necessarily stoichiometric.

Interrelated with this oxidation state limitation are the factors of dispersion of the tin component in the support and of particle size of the tin component. It has been established that it is only when the tin component is uniformly dispersed throughout the carrier material in a particle or crystallite size having a maximum dimension less than 100 Angstroms that it can successfully maintain its preferred oxidation state when it is subjected to a high temperature prereduction treatment or to hydrocarbon conversion conditions as hereinafter described. Thus it is an essential feature of our invention that the instant acidic multimetallic catalytic composite is prepared in a manner selected to meet the stated particle size and uniform dispersion limitations. By the use of the expression "uniform dispersion of a specified component in the carrier material" it is intended to described the situation where the concentration of the specified ingredient is approximately the same in any reasonably divisable portion of the carrier material. Similarly, the expression "particles or crystallites having a maximum dimension less than 100° A" is intended to denote particles that would pass through a sieve having a 100° A mesh size if it were possible to make such a sieve.

The tin component may be incorporated into the catalytic composite in any suitable manner known to effectively disperse this component throughout the carrier material in the required particle size. Thus this component may be added to the carrier by coprecipitation or cogellation of a suitable soluble tin salt with the carrier material, by ion-exchange of suitable tin ions contained in the carrier material when the ion exchange sites are uniformly distributed throughout the carrier or controlled impregnation of the carrier material with a suitable soluble tin salt under conditions selected to result in penetration of all sections of the carrier material by the tin component. One preferred method of incorporating the tin component involves coprecipitating or cogelling it during the preparation of the preferred carrier material, alumina. This method typically involves the addition of a suitable soluble tin compound such as stannous or stannic chloride to an alumina hydrosol, mixing these ingredients to obtain a uniform distribution of the tin moiety throughout the sol and then combining the hydrosol with a suitable gelling agent and dropping the resulting mixture into an oil bath etc., as explained in detail hereinbefore. After drying and calcining the resulting gelled carrier material there is obtained an intimate combination of alumina and tin oxide having the required dispersion and particle size. Another preferred method of incorporating the tin component into the catalytic composite involves utilization of a soluble, decomposable compound of tin to impregnate the porous carrier material. In general, the solvent used in this impregnation step is selected on the basis of the capability to dissolve the desired tin compound and to hold the tin moiety in solution until it is evenly distributed throughout the carrier material and is preferably an aqueous, rather strongly acidic solution. Thus the tin component may be added to the carrier material by commingling the latter with an aqueous solution of a suitable tin salt or suitable compound of tin such as stannous bromide, stannous chloride, stannic chloride, stannic chloride pentahydrate, stannic chloride diamine, stannic trichloride bromide, stannic chromate, stannous fluoride, stannic fluoride, stannic iodide, stannic sulfate, stannic tartrate and the like compounds. The acid used in the impregnation solution may be any organic or inorganic acid that is capable of maintaining the pH of the impregnation solution in the range of about -1 or less to about 3 and preferably less than 1 during the impregnation step and that does not contaminate the resultant catalyst. Suitable acids are: inorganic acids such as hydrochloric acid, nitric acid and the like; and strongly acidic organic acids such as oxalic acid, malonic acid, citric acid, malic acid, formic acid, tartaric acid, and the like. A particularly preferred impregnation solution comprises stannic or stannous chloride dissolved in a hydrochloric acid solution containing HCl in an amount corresponding to at least about 5 wt. % of the carrier material which is to be impregnated. Another useful impregnation solution is stannous or stannic chloride dissolved in an anhydrous alcohol such as ethanol. In general, the tin component can be incorporated either prior to, simultaneously with, or after the other metallic components are added to the carrier material. However, we have found that excellent results are obtained when the tin component is incoporated in the carrier material during its preparation and the other metallic components are added in a subsequent impregnation step after the tin-containing carrier material is calcined.

Regarding the amount of the tin component contained in the instant composite, it is preferably sufficient to constitute about 0.01 to about 5 wt. % of the final composite, calculated on an elemental basis, although substantially higher amounts of tin may be utilized in some cases. Best results are typically obtained with about 0.1 to about 2 wt. % tin.

A second essential ingredient of the subject catalyst is the platinum group component. This is, it is intended to cover the use of platinum, iridium, osmium, ruthenium, rhodium, palladium or mixtures thereof as a second component of the present composite. It is an essential feature of the present invention that substantially all of this platinum group component exists within the final catalytic composite in the elemental metallic state. Generally, the amount of this component present in the final catalytic composite is small compared to the quantities of the other components combined therewith. In fact, the platinum group component generally will comprise about 0.01 to about 2 wt. % of the final catalytic composite, calculated on an elemental basis. Excellent results are obtained when the catalyst contains about 0.05 to about 1 wt. % of platinum, iridium, rhodium or palladium metal. Particularly preferred mixtures of these metals are platinum and iridium and platinum and rhodium.

This platinum group component may be incorporated in the catalytic composite in any suitable manner known to result in a relatively uniform distribution of this component in the carrier material such as coprecipitation or cogellation, ion exchange or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chloropalladic acid. Other watersoluble compounds or complexes of platinum group metals may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, hexamminerhodium chloride, rhodium carbonylchloride, rhodium trichloride hydrate, rhodium nitrate, sodium hexachlororhodate (III), sodium hexanitrorhodate (III), iridium tribromide, iridium dichloride, iridium tetrachloride, sodium hexanitroiridate (III), potassium or sodium chloroiridate, potassium rhodium oxalate, etc. The utilization of a platinum, iridium, rhodium or palladium chloride compound, such as chloroplatinic, chloroiridic or chloropalladic acid or rhodium trichloride hydrate, is preferred since it facilitates the incorporation of both the platinum group components and at least a minor quantity of the halogen component in a single step. Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

A third essential ingredient of the acidic multimetallic catalytic composite of the present invention is a cobalt component. Although this component may be initially incorporated into the composite in many different decomposable forms which are hereinafter stated, our basic finding is that the catalytically active state for hydrocarbon conversion with this component is the elemental metallic state. Consequently, it is a feature of our invention that substantially all of the catalytically available cobalt component exists in the catalytic composite either in the elemental metallic state or in a state which is reducible to the elemental state under hydrocarbon conversion conditions. Examples of this last state are obtained when the cobalt component is initially present in the form of cobalt oxide, halide, oxyhalide, and the like reducible compounds. As a corollary to this basic finding on the active state of the cobalt component, it follows that the presence of cobalt in forms which are not reducible at hydrocarbon conversion conditions is to be scrupulously avoided if the full benefits of the present invention are to be realized. Illustrative of these undesired forms are cobalt sulfide and the cobalt oxysulfur compounds such as cobalt sulfate. Best results are obtained when the composite initially contains all of the cobalt component in the elemental metallic state or in a reducible oxide state or in a mixture of these states. All available evidence indicates that the preferred preparation procedure specifically described in Example I results in a catalyst having the cobalt component in a reducible oxide form. The cobalt component may be utilized in the composite in any amount which is catalytically effective, with the preferred amount being about 0.5 to about 5 wt. % thereof, calculated on an elemental cobalt basis. Typically, best results are obtained with about 0.5 to about 2 wt. % cobalt. It is, additionally, preferred to select the specific amount of cobalt from within this broad weight range as a function of the amount of the platinum group component, on an atomic basis, as is explained hereinafter.

The cobalt component may be incorporated into the catalytic composite in any suitable manner known to those skilled in the catalyst formulation art to result in a relatively uniform distribution of cobalt in the carrier material such as coprecipitation, cogellation, ion exchange, impregnation, etc. In addition, it may be added at any stage of the preparation of the composite — either during preparation of the carrier material or thereafter — since the precise method of incorporation used is not deemed to be critical. However, best results are obtained when the cobalt component is relatively uniformly distributed throughout the carrier material in a relatively small particle or crystallite size having a maximum dimension of less than 100 Angstroms, and the preferred procedures are the ones that are known to result in a composite having a relatively uniform distribution of the cobalt moiety in a relatively small particle size. One acceptable procedure for incorporating this component into the composite involves cogelling or coprecipitating the cobalt component during the preparation of the preferred carrier material, alumina. This procedure usually comprehends the addition of a soluble, decomposable, and reducible compound of cobalt such as cobalt chloride or nitrate to the alumina hydrosol before it is gelled. The resulting mixture is then finished by conventional gelling, aging, drying and calcination steps as explained hereinbefore. One preferred way of incorporating this component is an impregnation step wherein the porous carrier material is impregnated with a suitable cobalt-containing solution either before, during or after the carrier material is calcined or oxidized. The solvent used to form the impregnation solution may be water, alcohol, ether or any other suitable organic or inorganic solvent provided the solvent does not adversely interact with any of the other ingredients of the composite or interfere with the distribution and reduction of the cobalt component. Preferred impregnation solutions are aqueous solutions of water-soluble, decomposable, and reducible cobalt compounds such as cobaltous acetate, cobaltous benzoate, cobaltous bromate, cobaltous bromide, cobaltous chlorate and perchlorate, cobaltous chloride, cobaltic chloride, cobaltous fluoride, cobaltous iodide, cobaltous nitrate, hexamminecobalt (III) chloride, hexamminecobalt (III) nitrate, triethylenediamminecobalt (III) chloride, cobaltous hexamethylenetetramine, and the like compounds. Best results are ordinarily obtained when the impregnation solution is an aqueous solution of cobalt chloride or cobalt nitrate. This cobalt component can be added to the carrier material, either prior to, simultaneously with, or after the other metallic components are combined therewith. Best results are usually achieved when this component is added simulaneously with the platinum group component via an acidic aqueous impregnation solution. In fact, excellent results are obtained, as reported in the examples, with an impregnation procedure using an acidic aqueous solution comprising chloroplatinic acid, cobaltous chloride and hydrochloric acid.

As used herein, the expression "catalytically available cobalt" is intended to mean the portion of the cobalt component that is available for use in accelerating the particular hydrocarbon conversion reaction of interest. For certain types of carrier materials which can be used in the preparation of the instant catalytic composite, it has been observed that a portion of the cobalt incorporated therein is essentially bound-up in the crystal structure thereof in a manner which essentially makes it more a part of the refractory carrier material than a catalytically active component. Specific examples of this effect are observed when the carrier material can form a spinel or spinel-like structure with a portion of the cobalt component. When this effect occurs, it is only with great difficulty, that the portion of the cobalt bound-up with the support can be reduced to a catalytically active state and the conditions required to do this are beyond the severity levels normally associated with hydrocarbon conversion conditions and are in fact likely to seriously damage the necessary porous characteristics of the support. In the cases where cobalt can interact with the crystal structure of the support to render a portion thereof catalytically unavailable, the concept of the present invention merely requires that the amount of cobalt added to the subject catalyst be adjusted to satisfy the requirements of the support as well as the catalytically available cobalt requirements of the present invention. Against this background then, the hereinafter stated specifications for oxidation state and dispersion, of the cobalt component, are to be interpreted as directed to a description of the catalytically available cobalt. On the other hand, the specifications for the amount of cobalt used are to be interpreted to include all of the cobalt contained in the catalyst in any form.

It is essential to incorporate a halogen component into the acid multimetallic catalytic composite of the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g., as the chloride). This combined halogen may be either fluorine, chlorine, iodine, bromine, or mixtures thereof. Of these, fluorine and particularly chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the platinum group, cobalt or tin components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. For reforming, the halogen will be typically combined with the carrier material in an amount sufficient to result in a final composite that contains about 0.1 to about 3.5%, and preferably about 0.5 to about 1.5%, by weight, of halogen, calculated on an elemental basis. In isomerization or hydrocracking embodiments, it is generally preferred to utilize relatively larger amounts of halogen in the catalyst — typically ranging up to about 10 wt. % halogen calculated on an elemental basis, and more preferably, about 1 to about 5 wt. %. It is to be understood that the specified level of halogen component in the instant catalyst can be achieved or maintained during use in the conversion of hydrocarbons by continuously or periodically adding to the reaction zone a decomposable halogen-containing compound such as an organic chloride (e.g. ethylene dichloride, carbon tetrachloride, t-butyl chloride) in an amount of about 1 to 100 wt. ppm. of the hydrocarbon feed, and preferably about 1 to 10 wt. ppm.

Regarding especially preferred amounts of the various metallic components of the subject catalyst, we have found it to be a good practice to specify the amounts of the cobalt component and the tin component as a function of the amount of the platinum group component. On this basis, the amount of the cobalt component is ordinarily selected so that the atomic ratio of cobalt to platinum group metal contained in the composite is about 0.8:1 to about 66:1, with the preferred range being about 1.6:1 to about 18:1. Similarly, the amount of the tin component is ordinarily selected to produce a composite containing an atomic ratio of tin to platinum or palladium metal of about 0.1:1 to about 13:1, with the preferred range being about 0.3:1 to about 5:1.

Another significant parameter for the instant catalyst is the "total metals content" which is defined to be the sum of the platinum group component, the cobalt component and the tin component, calculated on an elemental basis. Good results are ordinarily obtained with the subject catalyst when this parameter is fixed at a value of about 0.15 to about 4 wt. %, with best results ordinarily achieved at a metals loading of about 0.3 to about 3 wt. %.

In embodiments of the present invention wherein the instant multimetallic catalytic composite is used for the dehydrogenation of dehydrogenatable hydrocarbons or for the hydrogenation of hydrogenatable hydrocarbons, it is ordinarily a preferred practice to include an alkali or alkaline earth metal component in the composite. More precisely, this optional ingredient is selected form the group consisting of the compounds of the alkali metals — cesium, rubidium, potassium, sodium, and lithium — and the compounds of the alkaline earth metals — calcium, strontium, barium and magnesium. Generally, good results are obtained in these embodiments when this component constitutes about 0.1 to about 5 wt. % of the composite, calculated on the elemental basis. This optional alkali or alkaline earth metal component can be incorporated in the composite in any of the known ways, with impregnation with an aqueous solution of a suitable water-soluble, decomposable compound being preferred.

An optional ingredient for the multimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith — for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride and the like compounds, with the aluminum halides and particularly aluminum chloride ordinarily yielding best results. Generally, this optional ingredient can be incorporated into the composite of the present invention by any of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a value selected from the range of about 1 to about 100 wt. % of the carrier material generally being preferred.

Regardless of the details of how the components of the catalyst are combined with the porous carrier material, the final catalyst generally will be dried at a temperature of about 200° to about 600° F. for a period of at least about 2 to about 24 hours or more, and finally calcined or oxidized at a temperature of about 700° F.

to about 1100° F. in an air or oxygen atmosphere for a period of about 0.5 to about 10 hours in order to convert substantially all of the metallic components to the corresponding oxide form. Because a halogen component is utilized in the catalyst, best results are generally obtained when the halogen content of the catalyst is adjusted during the oxidation step by including a halogen or a halogen-containing compound such as HCl in the air or oxygen atmosphere utilized. In particular, when the halogen component of the catalyst is chlorine, it is preferred to use a mole ratio of $H_2O$ to HCl of about 5:1 to about 100:1 during at least a portion of the oxidation step in order to adjust the final chlorine content of the catalyst to a range of about 0.1 to about 3.5 wt. %. Preferably, the duration of this halogenation step is about 1 to 5 hours.

The resultant oxidized catalytic composite is preferably subjected to a substantially water-free and hydrocarbon-free reduction step prior to its use in the conversion of hydrocarbons. This step is designed to selectively reduce the platinum group component to the elemental metallic state and to insure a uniform and finely divided dispersion of the metallic components throughout the carrier material, while maintaining the tin component in a positive oxidation state. Preferably substantially pure and dry hydrogen (i.e. less than 20 vol. ppm. $H_2O$) is used as the reducing agent in this step. The reducing agent is contacted with the oxidized catalyst at conditions including a reduction temperature of about 800° F. to about 1200° F. and a period of time of about 0.5 to 10 hours effective to reduce substantially all of the platinum group component to the elemental metallic state while maintaining the tin component in an oxidation state above that of the elemental metal. Quite surprisingly, we have found that if this reduction step is preformed with a hydrocarbon-free hydrogen stream at the temperature indicated and if the cobalt component is properly distributed in the carrier material in the oxide form and in the specified particle size, no substantial amount of the cobalt component will be reduced in this step. However, once the catalyst sees a mixture of hydrogen and hydrocarbon, a considerable fraction of the cobalt component is quickly reduced at the specified reduction temperature range. This reduction treatment may be performed in situ as part of a start-up sequence if precautions are taken to predry the plant to a substantially water-free state and if substantially water-free and hydrocarbon-free hydrogen is used.

The resulting catalytic composite is, in accordance with the basic concept of the present invention, preferably maintained in a sulfur-free state both during its preparation and thereafter during its use in the conversion of hydrocarbons. As indicated previously, the beneficial interaction of the cobalt component with the other ingredients of the present catalytic composite is contingent upon the maintenance of the cobalt moiety in a highly dispersed, readily reducible state in the carrier material. Sulfur in the form of adversely interfers with both the dispersion and reducibility of the cobalt component and consequently it is a highly preferred practice to avoid presulfiding the reduced acidic multimetallic resulting from the reduction step. Once the catalyst has been exposed to hydrocarbon for a sufficient period of time to lay down a protective layer of carbon or coke on the surface thereof, the sulfur sensitivity of the resulting carbon-containing composite changes rather markedly and the presence of small amounts of sulfur can be tolerated without permanently disabling the catalyst. The exposure of the freshly reduced catalyst to sulfur can seriously damage the cobalt component thereof and consequently jeopardize the superior performance characteristics associated therewith. However, once a protective layer of carbon is established on the catalyst, the sulfur deactivation effect is less permanent and sulfur can be purged therefrom by exposure to a sulfur-free hydrogen stream at a temperature of about 800° to 1100° F.

According to the present invention, a hydrocarbon charge stock and hydrogen are contacted with the instant acidic multimetallic catalyst in a hydrocarbon conversion zone. This contacting may be accomplished by using the catalyst in a fixed bed system, a moving bed system, a fluidized bed system, or in a batch type operation; however, in view of the danger of attrition losses of the valuble catalyst and of well known operational advantages, it is preferred to use either a fixed bed system or a dense-phase moving bed system such as is shown in U.S. Pat. No. 3,725,249. In a fixed bed system, a hydrogen-rich gas and the charge stock are preheated by any suitable heating means to the desired reaction temperature and then are passed into a conversion zone containing a fixed bed of the acidic multimetallic catalyst. It is, of course, understood that the conversion zone may be one or more separate reactors with suitable means therebetween to insure that the desired conversion temperature is maintained at the entrance to each reactor. It is also important to note that the reactants may be contacted with the catalyst bed in either upward, downward or radial flow fashion with the latter being preferred. In addition, the reactants may be in the liquid phase, a mixed liquid-vapor phase, or a vapor phase when they contact the catalyst, with best results obtained in the vapor phase.

In the case where the acidic multimetallic catalyst of the present invention is used in a reforming operation, the reforming system will typically comprise a reforming zone containing one or more fixed beds or dense-phase moving beds of the catalyst. This reforming zone may be one or more separate reactors with suitable heating means therebetween to compensate for the endothermic nature of the reactants that take place in each catalyst bed. The hydrocarbon feed stream that is charged to this reforming system will comprise hydrocarbon fractions containing naphthenes and paraffins that boil within the gasoline range. The preferred charge stocks are those consisting essentially of naphthenes and paraffins, although in some cases aromatics and/or olefins may also be present. This preferred class includes straight run gasolines, natural gasolines, synthetic gasolines and the like. On the other hand, it is frequently advantageous to charge thermally or catalytically cracked gasolines or higher boiling fractions thereof. Mixtures of straight run and cracked gasolines can also be used to advantage. The gasoline charge stock may be a full boiling gasoline having an initial boiling point of from about 50° to about 150° F. and an end boiling point within the range of from about 325° to about 425° F., or may be a selected fraction thereof which generally will be a higher boiling fraction commonly referred to as a heavy naphtha — for example, a naphtha boiling in the range of $C_7$ to 400° F. In some cases, it is also advantageous to charge pure hydrocarbons or mixtures of hydrocarbons that have been extracted from hydrocarbon distillates — for example, straight-chain paraffins — which are to be converted to aromatics. It is preferred that these charge stocks be treated by conventional catalytic pretreatment methods such as hydrorefining, hydrotreating, hydrodesulfurization, etc., to remove substantially all sulfurous, nitrogenous and water-yielding contaminants therefrom and to saturate any olefins that may be contained therein.

In other hydrocarbon conversion embodiments, the charge stock will be of the conventional type customarily used for the particular kind of hydrocarbon conversion being effected. For example, in a typical isomerization embodiment the charge stock can be a paraffinic stock rich in $C_4$ to $C_8$ normal paraffins, or a normal butane-rich stock, or a n-hexane-rich stock, or a mixture of xylene isomers, etc. In a dehydrogenation embodiment, the charge stock can be any of the known dehydrogenatable hydrocarbons such as an aliphatic compound containing 2 to 30 carbon atoms per molecule, a $C_4$ to $C_{30}$ normal paraffin, a C8 to $C_{12}$ alkylaromatic, a naphthene and the like. In hydrocracking embodiments, the charge stock will be typically a gas oil, heavy cracked cycle oil, etc. In addition, alkylaromatic and naphthenes can be conveniently isomerized by using the catalyst of the present invention. Likewise, pure hydrocarbons or substantially pure hydrocarbons can be converted to more valuable products by using the acidic multimetallic catalyst of the present invention in any of the hydrocarbon conversion processes, known to the art, that use a dual-function catalyst.

Since sulfur has a high affinity for cobalt at hydrocarbon conversion conditions, we have found that best results are achieved in the conversion of hydrocarbons with the instant acidic multimetallic catalytic composite when the catalyst is used in a substantially sulfur-free environment. This is particularly true in the catalytic reforming embodiment of the present invention. The expression "substantially sulfur-free environment" is intended to mean that the total amount (expressed as equivalent elemental sulfur) of sulfur or sulfur-containing compounds, which are capable of producing a metallic sulfide at the reaction conditions used, entering the reaction zone containing the instant catalyst from any source is continuously maintained at an amount equivalent to less than 10 wt. ppm of the hydrocarbon charge stock, more preferably less than 5 wt. ppm, and most preferably less than 1 wt. ppm. Since in the ordinary operation of a conventional catalytic reforming process, wherein influent hydrogen is autogenously produced, the prime source for any sulfur entering the reforming zone is the hydrocarbon charge stock, maintaining the charge stock substantially free of sulfur is ordinarily sufficient to ensure that the environment containing the catalyst if maintained in the substantially sulfur-free state. More specifically, since hydrogen is a by-product of the catalytic reforming process, ordinarily the input hydrogen stream required for the process is obtained by recycling a portion of the hydrogen-rich stream recovered from the effluent withdrawn from the reforming zone. In this typical situation, this recycle hydrogen stream will ordinarily be substantially free of sulfur if the charge stock is maintained free of sulfur. If autogenous hydrogen is not utilized, then of course the concept of the present invention requires that the input hydrogen stream be maintained substantially sulfur-free; that is, less than 10 vol. ppm of $H_2S$, preferably less than 5 vol. ppm, and most preferably less than 1 vol. ppm.

The only other possible sources of sulfur that could interfere with the performance of the instant catalyst are sulfur that is initially combined with the catalyst and/or with the plant hardware. As indicated hereinbefore, a highly preferred feature of the present acidic multimetallic catalyst is that it is maintained substantially sulfur-free; therefore, sulfur released from the catalyst is not usually a problem in the present process. Hardware sulfur is ordinarily not present in a new plant; it only becomes a problem when the present process is to be implemented in a plant that has been service with a sulfur-containing feedstream. In this latter case, the preferred practice of the present invention involves an initial pre-treatment of the sulfur-containing plant in order to remove substantially all of the decomposable hardware sulfur therefrom. This can be easily accomplished by any of the techniques for stripping sulfur from hardware known to those in the art; for example, by the circulation of a substantially sulfur-free hydrogen stream through the internals of the plant at a relatively high temperature of about 800° to about 1200° F. until the $H_2S$ content of the effluent gas stream drops to a relatively low level — typically, less than 5 vol. ppm and preferably less than 2 vol. ppm. In sum, the preferred sulfur-free feature of the present invention requires that the total amount of detrimental sulfur entering the hydrocarbon conversion zone containing the hereinbefore described acidic multimetallic catalyst must be continuously maintained at a substantially low level; specifically, the amount of sulfur must be held to a level equivalent to less than 10 wt. ppm, and preferably less than 1 wt. ppm, of the feed.

In the case where the sulfur content of the feed stream for the present process is greater than the amounts previously specified, it is, of course, necessary to treat the charge stock in order to remove the undesired sulfur contaminants therefrom. This is easily accomplished by using any one of the conventional catalytic pre-treatment methods such as hydrorefining, hydrotreating, hydrodesulfurization, and the like to remove substantially all sulfurous, nitrogenous and water-yielding contaminants from this feedstream. Ordinarily, this involves subjecting the sulfur-containing feedstream to contact with a suitable sulfur-resistant hydrorefining catalyst in the presence of hydrogen under conversion conditions selected to decompose sulfur contaminants contained therein and form hydrogen sulfide. The hydrorefining catalyst typically comprises one or more of the oxides or sulfides of the transition metals of Groups VI and VIII of the Periodic Table. A particularly preferred hydrorefining catalyst comprises a combination of a metallic component from the iron group metals of Group VIII and of a metallic component of the Group VI transition metals combined with a suitable porous refractory support. Particularly good results have been obtained when the iron group component is cobalt and/or nickel and the Group VI transition metal is molybdenum or tungsten. The preferred support for this type of catalyst is a refractory inorganic oxide of the type previously mentioned. For example, good results are obtained with a hydrorefining catalyst comprising cobalt oxide and molybdenum oxide supported on a carrier material comprising alumina and silica. The conditions utilized in this hydrorefining step are ordinarily selected from the following ranges: a temperature of about 600° to about 950° F., a pressure of about 500 to about 5000 psig., a liquid hourly space velocity of about 1 to about 20 hr.$^{-1}$, and a hydrogen circulation rate of about 500 to about 10,000 standard cubic feet of hydrogen per barrel of charge. After this hydrorefining step, the hydrogen sulfide, ammonia and water liberated therein, are then easily removed from the resulting purified charge stock by conventional means such as a suitable stripping operation. Specific hydrorefining conditions are selected from the ranges given above as a function of the amounts and kinds of the sulfur contaminants in the feedstream in order to produce a substantially sulfur-free charge stock which is then charged to the process of the present invention.

In a reforming embodiment, it is generally preferred to utilize the novel acidic multimetallic catalytic composite in a substantially water-free environment. Essential to the achievement of this condition in the reforming zone is the control of the water level present in the charge stock and the hydrogen stream which is being charged to the zone. Best results are ordinarily obtained when the total amount of water entering the conversion zone from any source is held to a level less than 20 ppm and preferably less than 5 ppm expressed as weight of equivalent water in the charge stock. In general, this can be accomplished by careful control of the water present in the charge stock and in the hydrogen stream. The charge stock can be dried by using any suitable drying means known to the art, such as a conventional solid adsorbent having a high selectivity for water, for instance, sodium or calcium crystalline alumino-silicates, silica gel, activated alumina, molecular sieves, anhydrous calcium sulfate, high surface area sodium and the like adsorbents. Similarly, the water content of the charge stock may be adjusted by suitable stripping operations in a fractionation column or like device. And in some cases, a combination of adsorbent drying and distillation drying may be used advantageously to effect almost complete removal of water from the charge stock. In an especially preferred mode of operation, the charge stock is dried to a level corresponding to less than 5 wt. ppm. of $H_2O$ equivalent. In general, it is preferred to maintain the hydrogen stream entering the hydrocarbon conversion zone at a level of about 10 vol. ppm of water or less and most preferably about 5 vol. ppm or less. If the water level in the hydrogen stream is too high, drying of same can be conveniently accomplished by contacting the hydrogen stream with a suitable desiccant such as those mentioned above.

In the reforming embodiment, an effluent stream is withdrawn from the reforming zone and passed through a cooling means to a separation zone, typically maintained at about 25° to 150° F., wherein a hydrogen-rich gas stream is separated from a high octane liquid product stream, commonly called an unstabilized reformate. When the water level in the hydrogen stream is outside the range previously specified, at least a portion of this hydrogen-rich gas stream is withdrawn from the separating zone and passed through an adsorption zone containing an adsorbent selective for water. The resultant substantially water-free hydrogen stream can then be recycled through suitable compressing means back to the reforming zone. The liquid phase from the separating zone is typically withdrawn and commonly treated in a fractionating system in order to adjust the butane concentration, thereby controlling front-end volatility of the resulting reformate.

The conditions utilized in the numerous hydrocarbon conversion embodiments of the present invention are in general those customarily used in the art for the particular reaction, or combination of reactions, that is to be effected. For instance, alkylaromatic and paraffin isomerization conditions include: a temperature of about 32° F. to about 1000° F. and preferably from about 75° F. to about 600° F.; a pressure of atmospheric to about 100 atmospheres; a hydrogen to hydrocarbon mole ratio of about 0.5:1 to about 20:1 and an LHSV (calculated on the basis of equivalent liquid volume of the charge stock contacted with the catalyst per hour divided by the volume of conversion zone containing catalyst) of about 0.2 hr.$^{-1}$ to 10 hr.$^{-1}$. Dehydrogenation conditions include: a temperature of about 700° to about 1250° F., a pressure of about 0.1 to about 10 atmospheres, a liquid hourly space velocity of about 1 to 40 hr.$^{-1}$ and a hydrogen to hydrocarbon mole ratio of about 1:1 to 20:1. Likewise, typically hydrocracking conditions include: a pressure of about 500 psig. to about 3000 psig., a temperature of about 400° F. to about 900° F., an LHSV of about 0.1 hr.$^{-1}$ to about 10 hr.$^{-1}$, and hydrogen circulation rates of about 1000 to 10,000 SCF per barrel of charge.

In the reforming embodiment of the present invention, the pressure utilized is selected from the range of about 0 psig. to about 1000 psig., with the preferred pressure being about 50 psig. to about 600 psig. Particularly good results are obtained at low or moderate pressure; namely, a pressure of about 100 to 450 psig. In fact, it is a singular advantage of the present invention that it allows stable operation at lower pressure than have heretofore been successfully utilized in so-called continuous reforming system (i.e. reforming for periods of about 15 to about 200 or more barrles of charge per pound of catalyst without regeneration) with all platinum monometallic catalyst. In other words, the acidic multimetallic catalyst of the present invention allows the operation of a continuous reforming system to be conducted at lower pressure (i.e. 100 to about 350 psig.) for about the same or better catalyst cycle life before regeneration as has been heretofore realized with conventional monometallic catalysts at higher pressure (i.e. 400 to 600 psig.). On the other hand, the extraordinary activity and activity-stability characteristics of the catalyst of the present invention enables reforming conditions conducted at pressures of 400 to 600 psig. to achieve substantially increased catalyst cycle life before regeneration.

The temperature required for reforming with the instant catalyst is markedly lower than that required for a similar reforming operation using a high quality catalyst of the prior art. This significant and desirable feature of the present invention is a consequence of the extraordinary activity of the acidic multimetallic catalyst of the present invention for the octane-upgrading reactions that are preferably induced in a typical reforming operation. Hence, the present invention requires a temperature in the range of from about 800° F. to about 1100° F. and preferably about 900° F. to about 1050° F. As is well known to those skilled in the continuous reforming art, the initial selection of the temperature within this broad range is made primarily as a function of the desired octane of the product reformate considering the characteristics of the charge stock and of the catalyst. Ordinarily, the temperature then is thereafter slowly increased during the run to compensate for the inevitable deactivation that occurs to provide a constant octane product. Therefore, it is a feature of the present invention that not only is the initial temperature requirement substantially lower but also the rate at which the temperature is increased in order to maintain a constant octane product is substantially lower for the catalyst of the present invention than for an equivalent operation with a high quality reforming catalyst which is manufactured in exactly the same manner as the catalyst of the present invention except for the inclusion of the cobalt and tin components. Moreover, for the catalyst of the present invention, the $C_5+$ yield loss for a given temperature increase is substantially lower than for a high quality reforming catalyst of the prior art. The extraordinary activity of the instant catalyst can be utilized in a number of highly beneficial ways to enable increased performance of a catalytic reforming process relative to that obtained in a similar operation with a monometallic or bimetallic catalyst of the prior art, some of these are: (1) Octane number of $C_5+$ product can be substantially increased without sacrificing catalyst run length. (2) The duration of the process operation before regeneration, becomes necessary, can be significantly increased (i.e. catalyst run length or cycle life). (3) $C_5+$ yield can be increased by lowering average reactor pressure with no change in catalyst run length. (4) Investment costs can be lowered without any sacrifice in cycle life by lowering recycle gas requirements thereby saving on capital cost for compressor capacity or by lowering initial catalyst loading requirements thereby saving on cost of catalyst and on capital cost of the reactors. (5) Throughput can be increased sharply at no sacrifice in catalyst cycle life if sufficient heater capacity is available.

The reforming embodiment of the present invention also typically utilizes sufficient hydrogen to provide an amount of about 1 to about 20 moles of hydrogen per mole of hydrocarbon entering the reforming zone, with excellent results being obtained when about 2 to about 6 moles of hydrogen are used per mole of hydrocarbon. Likewise, the liquid hourly space velocity (LHSV) used in reforming is selected from the range of about 0.1 to about 10 hr.$^{-1}$, with a value in the range of about 1 to about 5 hr.$^{-1}$ being preferred. In fact, it is a feature of the present invention that it allows operations to be conducted at higher LHSV than normally can be stably achieved in a continuous reforming process with a high quality reforming catalyst of the prior art. This last feature is of immense economic significance because it allows a continuous reforming process to operate at the same throughput level with less catalyst inventory or at greatly increased throughput level with the same catalyst inventory than that heretofore used with conventional reforming catalysts at no sacrifice in catalyst life before regeneration.

The following examples are given to illustrate further the preparation of the acidic multimetallic catalytic composite of the present invention and the use thereof in the conversion of hydrocarbons. It is understood that the examples are intended to be illustrative rather than restrictive. Specific operating conditions, processing techniques, particular catalytic composites and other individual process details will be given in the following detailed description of several of the hydrocarbon hydroprocesses to which the present invention is applicable. These will be presented by way of examples given in conjunction with commercially-scaled operating units. In presenting these examples, it is not intended that the invention be limited to the specific illustrations, nor is it intended that a given process be limited to the particular operating conditions, catalytic composite, processing techniques, charge stock, etc. It is understood, therefor, that the present invention is merely illustrated by the specifics hereinafter set forth.

EXAMPLE I

A tin-containing alumina carrier material comprising 1/16 inch spheres was prepared by: forming an aluminum hydroxyl chloride sol by dissolving substantially pure aluminum pellets in a hydrochloric acid solution, addin stannic chloride to the resulting sol in an amount selected to result in a finished catalyst containing about 0.2 wt. % tin, adding hexamethylenetetramine to the resulting tin-containing alumina sol, gelling the resulting solution by dropping it into an oil bath to form spherical particles of an aluminum- and tin-containing hydrogel, aging and washing the resulting particles and finally drying and calcining the aged and washed particles to form spherical particles of gamma-alumina containing a uniform dispersion of about 0.2 wt. % tin in the form of tin oxide and about 0.3 wt. % combined chloride. Additional details as to this method of preparing the preferred gamma-alumina carrier material are given in the teachings of U.S. Pat. No. 2,620,314.

An aqueous impregnation solution containing chloroplatinic acid, cobaltous chloride and hydrogen chloride was then prepared. The tin-containing alumina carrier material was thereafter admixed with the impregnation solution. The amount of reagents contained in this impregnation solution was calculated to result in a final composite containing, on an elemental basis, 0.30 wt. % platinum and 1.0 wt. % cobalt. In order to insure uniform dispersion of the metallic components throughout the carrier material, the amount of hydrochloric acid used was about 3 wt. % of the alumina particles. This impregnation step was performed by adding the carrier material particles to the impregnation mixture with constant agitation. In addition, the volume of the solution was approximately the same as the void volume of the carrier material particles. The impregnation mixture was maintained in contact with the carrier material particles for a period of about ½ to about 3 hours at a temperature of about 70° F. Thereafter, the temperature of the impregnation mixture was raised to about 225° F. and the excess solution was evaporated in a period of about 1 hour. The resulting dried impregnated particles were then subjected to an oxidation treatment in a dry air stream at a temperature of about 975° F. and a GHSV of about 500 hr.$^{-1}$ for about ½ hour. This oxidation step was designed to convert substantially all of the metallic ingredients to the corresponding oxide forms. The resulting oxidized spheres were subsequently contacted in a halogen treating step with an air stream containing $H_2O$ and HCl in a mole ratio of about 30:1 for about 2 hours at 975° F. and a GHSV of about 500 hr.$^{-1}$ in order to adjust the halogen content of the catalyst particles to a value of about 1.09 wt. %. The halogen-treated spheres were thereafter subjected to a second oxidation step with a dry air stream at 975° F. and a GHSV of 500 hr.$^{-1}$ for an additional period of about ½ hour.

The oxidized and halogen treated catalyst particles were then subjected to a dry pre-reduction treatment, designed to reduce the platinum component to the elemental state while maintaining the tin component in a positive oxidation state, by contacting it for about 1 hour with a substantially hydrocarbon-free dry hydrogen stream containing less than 5 vol. ppm $H_2O$ at a temperature of about 1050° F., a pressure slightly above atmospheric, and a flow rate of the hydrogen stream through the catalyst particles corresponding to a gas hourly space velocity of about 400 hr.$^{-1}$.

Examination of a sample of the resulting reduced catalyst by electron spin resonance techniques indicated that substantially all of the platinum component had been reduced whereas substantially all of the tin component remained in the tin oxide state. Likewise controlled reduction experiments along with additional evidence from electron spin resonance established that at the completion of this reduction step, substantially all of the cobalt component was in a readily reducible oxide form. X-ray and electron spin resonance studies of the cobalt crystallites contained in the instant catalyst after it had been exposed to hydrocarbons during the subsequently described reforming operation indicated that substantially all of the cobalt component was reduced to the elemental metallic state at the reforming conditions utilized.

A sample of the resulting reduced catalyst particles was analyzed and found to contain, on an elemental basis, about 0.30 wt. % platinum, about 1.0 wt. % cobalt, about 0.2 wt. % tin and about 1.09 wt. % chloride. This corresponds to an atomic ratio of tin to platinum of 1.1:1 and to an atomic ratio of cobalt to platinum of 11:1.

EXAMPLE II

In this example, the present invention is illustrated as applied to the hydrogenation of aromatic hydrocarbons such as benzene, toluene, the various xylenes, naphthalenes, etc., to form the corresponding cyclic paraffins. The corresponding cyclic paraffins, resulting from the hydrogeneration of the aromatic nuclei, include compounds such as cyclohexane, mono-, di-, tri-substituted cyclohexanes, decahydronaphthalene, tetrahydronaphthalene, etc., which find widespread use in a variety of commercial industries in the manufacture of nylon, as solvents for various fats, oils, waxes, etc.

Aromatic concentrates are obtained by a multiplicity of techniques. For example, a benzene-containing fraction may be subjected to distillation to provide a heart-cut which contains the benzene. This is then subjected to a solvent extraction process which separates the benzene from the normal or iso-paraffinic components, and the naphthenes contained therein. Benzene is readily recovered from the selected solvent by way of distillation, and in a purity of 99.0% or more. In accordance with the present process, the benzene is hydrogenated in contact with a nonacidic catalytic composite containing 0.01 to about 2.0% by weight of a platinum metal group component, from about 0.01 to about 5.0% by weight of a tin component, from about 0.01 to about 5% by weight of a cobalt component and from about 0.01 to about 1.5% by weight of an alkalinous metal component. Operating conditions include a maximum catalyst bed temperature in the range of about 200° F. to about 800° F., a pressure of from 500 to about 2,000 psig., a liquid hourly space velocity of about 1.0 to about 10.0 and a hydrogen circulation rate in an amount sufficient to yield a mole ratio of hydrogen to cyclohexane, in the product effluent from the last reaction zone, not substantially less than about 4.0:1. Although not essential, one preferred operating technique involves the use of three reaction zones, each of which contains approximately one-third of the total quantity of catalyst employed. The process is further facilitated when the total fresh benzene is added in three approximately equal portions, one each to the inlet of each of the three reaction zones.

The catalyst utilized is an alumina carrier material combined with about 4% by weight of tin, 4% by weight of coblat, 0.375% by weight of platinum, and about 0.90% by weight of lithium, all of which are calculated on the basis of the elemental metals. The hydrogenation process will be described in connection with a commercially-scaled unit having a total fresh benzene feed capacity of about 1,488 barrels per day. Makeup gas in an amount of about 741.6 mols/hr. together with hydrogen recovered from the reactor effluent is admixed with 2,396 Bbl./day (about 329 mols/hr.) of a cyclohexane cycle stream, the mixture being at a temperature of about 137° F., and further mixed with 96.24 mols/hr. (582 Bbl./day) of the benzene feed; the final mixture constitutes the total charge to the first reaction zone.

Following suitable heat-exchange with various hot effluent streams, the total feed to the first reaction zone is at a temperature of 385° F. and a pressure of 460 psig. The reaction zone effluent is at a temperature of 606° F. and a pressure of about 450 psig. The total effluent from the first reaction zone is utilized as a heat-exchange medium, in a stream generator, whereby the temperature is reduced to a level of about 545° F. The cooled effluent is admixed with about 98.5 moles per hour (596 Bbl./day) of fresh benzene feed, at a temperature of 100° F.; the resulting temperature is 400° F., and the mixture enters the second reaction zone at a pressure of about 440 psig. The second reaction zone effluent, at a pressure of 425 psig. and a temperature of 611° F., is admixed with 51.21 mols/hr. (310 Bbl./day) of fresh benzene feed, the resulting mixture being at a temperature of 578° F. Following its use as a heat-exchange medium, the temperature is reduced to 400° F., and the mixture enters the third reaction zone at a pressure of 415 psig. The third reaction zone effluent is at a temperature of about 500° F. and a pressure of about 400 psig. Through utilization as a heat-exchange medium, the temperature is reduced to a level of about 244° F., and subsequently reduced to a level of about 115° F. by use of an air-cooled condenser. The cooled third reaction zone effluent is introduced into a high pressure separator, at a pressure of about 370 psig.

A hydrogen-rich vaporous phase is withdrawn from the high pressure separator and recycled by way of compressive means, at a pressure of about 475 psig., to the inlet of the first reaction zone. A portion of the normally liquid phase is recycled to the first reaction zone as the cyclohexane concentrate hereinbefore described. The remainder of the normally liquid phase is passed into a stabilizing column functioning at an operating pressure of about 250 psig., a top temperature of about 160° F. and a bottom temperature of about 430° F. The cyclohexane product is withdrawn from the stabilizer as a bottoms stream, the overhead stream being vented to fuel. The cyclohexane concentrate is recovered in an amount of about 245.80 moles per hour, of which only about 0.60 moles per hour constitutes other hexanes. In brief summation then, from the 19,207 pounds per hour of fresh benzene feed, 20,685 pounds per hour of cyclohexane product is recovered.

EXAMPLE III

Another hydrocarbon hydroprocessing scheme, to which the present invention is applicable, involves the hydrorefining of coke-forming hydrocarbon distillates. The hydrocarbon distillates generally contain mono-olefinic, di-olefinic and aromatic hydrocarbons. Through the utilization of a catalytic composite comprising a tin component, a cobalt component and a platinum group metal component, increased selectivity and stability of operation is obtained; selectivity is most noticeable with respect to the retention of aromatics, and in hydrogenating conjugated di-olefinic and mono-olefinic hydrocarbons. Such charge stocks generally result from diverse conversion processes including the catalytic and/or thermal cracking of petroleum, sometimes referred to as pyrolysis, the destructive distillation of wood or coal, shale oil retorting, etc. The impurities in these distillate fractions must necessarily be removed before the distillates are suitable for their intended use, or which when removed, enhance the value of the distillate fraction for further processing. Frequently, it is intended that these charge stocks be saturated to the extent necessary to remove the conjugated di-olefins, while simultaneously retaining the aromatic hydrocarbons. When subjected to hydrorefining for the purpose of removing the contaminating influences, there is encountered difficulty in effecting the desired degree of reaction due to the formation of coke and other carbonaceous material.

As utilized herein, hydrogenating is intended to be synonymous with hydrorefining. The purpose is to provide a highly selective and stable process for hydrogenating coke-forming hydrocarbon distillates, and this is accomplished through the use of a fixed-bed catalytic reaction system utilizing a catalyst comprising a tin component, a cobalt component, and a platinum group metal component. There exists two separate, desirable routes for the treatment of coke-forming distillates, for example a pyrolysis naphtha by-product. One such route is directed toward a product suitable for use in certain gasoline blending. With this as the desired object, the process can be effected in a single stage, or reaction zone, with the catalytic composite hereinafter specifically described as the first-stage catalyst. The attainable selectivity in this instance resides primarily in the hydrogenation of highly reactive double bonds. In the case of conjugated di-olefins, the selectivity afforded restricts the hydrogenation to produce mono-olefins, and, with respect to the styrenes, for example, the hydrogenation is inhibited to produce alkyl benzenes without ring saturation. The selectivity is accomplished with a minimum of polymer would necessitate a re-running of the product before blending to gasoline would be feasible. It must be noted that the mono-olefins, whether virgin, or products of di-olefin partial saturation, are unchanged in the single, or first-stage reaction zone. Where however the desired end result is aromatic hydrocarbon retention, intended for subsequent extraction, the two-stage route is required. The mono-olefins must be substantially saturated in the second stage to facilitate aromatic extraction by way of currently utilized methods. Thus, the desired necessary hydrogenation involves saturation of the mono-olefins. Attendant upon this is the necessity to avoid even partial saturation of aromatic nuclei.

With respect to one catalytic composite, its principal function involves the selective hydrogenation of conjugated diolefinic hydrocarbons to mono-olefinic hydrocarbons. The catalytic composite comprises an alumina-containing refractory inorganic oxide, a tin component, a cobalt component, a platinum group metal component and an alkali-metal component, the latter being preferably potassium and/or lithium. Through the utilization of a particular sequence of processing steps, and the use of the foregoing described catalyst composites, the formation of high molecular weight polymers and co-polymers is inhibited to a degree which permits processing for an extended period of time. Briefly, this is accomplished by initiating the hydrorefining reactions at temperatures below about 500° F., at which temperatures the coke-forming reactions are not promoted.

The hydrocarbon distillate charge stock, for example a light naphtha by-product from a commercial cracking unit designed and operated for the production of ethylene, having a gravity of about 34.0° API, a bromine number of about 35.0, a diene value of about 17.5 and containing 75.9 vol. % aromatic hydrocarbons, is admixed with recycled hydrogen. This light naphtha co-product has an initial boiling point of about 164° F. and an end boiling point of about 333° F. The hydrogen circulation rate is within the range of from about 1,000 to about 10,000 scf./Bbl., and preferably in the narrower range of from 1,500 to about 6,000 scf./Bbl. The charge stock is heated to a temperature such that the maximum catalyst temperature is in the range of from about 200° F. to about 500° F., by way of heat-exchange with various product effluent streams, and is introduced into the first reaction zone at an LHSV in the range of about 0.5 to about 10.0. The reaction zone is maintained at a pressure of from 400 to about 1,000 psig., and preferably at a level in the range of from 500 psig. to about 900 psig.

The temperature of the product effluent from the first reaction zone is increased to a level above about 500° F., and preferably to result in a maximum catalyst temperature in the range of 600° F. to 900° F. The saturation of mono-olefins, contained within the first zone effluent, is effected in the second zone. When the process is functioning efficiently, the diene value of the liquid charge entering the second catalytic reaction zone is less than about 1.0 and often less than about 0.3. The second catalytic reaction zone is maintained under an imposed pressure of from about 400 to about 1,000 psig., and preferably at a level of from about 500 to about 900 psig. The two-stage process is facilitated when the focal point for pressure control is the high pressure separator serving to separate the product effluent from the second catalytic reaction zone. It will, therefore, be maintained at a pressure slightly less than the first catalytic reaction zone, as a result of fluid flow through the system. The LHSV through the second reaction zone is about 0.5 to about 10.0, based upon fresh feed only. The hydrogen circulation rate will be in a range of from 1,000 to about 10,000 scf./Bbl., and preferably from about 1,000 to about 8,000 scf./Bbl. Series-flow through the entire system is facilitated when the recycle hydrogen is admixed with the fresh hydrocarbon charge stock. Make-up hydrogen, to supplant that consumed in the overall process, may be introduced from any suitable external source, but is preferably introduced into the system by way of the effluent line from the first catalytic reaction zone to the second catalytic reaction zone.

With respect to the naphtha boiling range portion of the product effluent, the aromatic concentration is about 75.1% by volume, the bromine number is less than about 0.3 and the diene value is essential nil.

With charge stocks having exceedingly high diene values, a recycle diluent is employed in order to prevent an excessive temperature rise in the reaction system. Where so utilized, the source of the diluent is preferably a portion of the normally liquid product effluent from the second catalytic reaction zone. The precise quantity of recycle material material varies from feed stock to feed stock; however, the rate at any given time is controlled by monitoring the diene value of the combined liquid feed to the first reaction zone. As the diene value exceeds a level of about 25.0, the quantity of recycle is increased, thereby increasing the combined liquid feed ratio; when the diene value approaches a level of about 20.0, or less, the quantity of recycle diluent may be lessened, thereby decreasing the combined liquid feed ratio.

EXAMPLE IV

This illustration of a hydrocarbon hydroprocessing scheme, encompassed by our invention is one which involves hydrocracking heavy hydrocarbonaceous material into lower-boiling hydrocarbon products. In this instance, the preferred catalysts contain a tin component, a platinum group metal component, a cobalt component, and a halogen component combined with a crystalline aluminosilicate-carrier material, preferably faujasite, and still more preferably one which is at least 90.0% by weight zeolitic.

Most of the virgin stocks, intended for hydrocracking, are contaminated by sulfurous compounds and nitrogenous compounds, and, in the case of the heavier charge stocks, various metallic contaminants, insoluble asphalts, etc. Contaminated charge stocks are generally hydrorefined in order to prepare a charge suitable for hydrocracking. Thus, the catalytic process of the present invention can be beneficially utilized as the second stage of a two-stage process, in the first stage of which the fresh feed is hydrorefined.

Hydrocracking reactions are generally effected at elevated pressures in the range of about 800 to about 5,000 psig., and preferably at some intermediate level of 1,000 to about 3,500 psig. Liquid hourly space velocities of about 0.25 to about 10.0 will be suitable, the lower range generally reserved for the heavier stocks. The hydrogen circulation rate will be at least about 3,000 scf./Bbl., with an upper limit of about 50,000 scf./Bbl., based upon fresh feed. For the majority of feed stocks, hydrogen circulation in the range of 5,000 to 20,000 scf./Bbl. will suffice. With respect to the LHSV, it is based upon fresh feed, notwithstanding the use of recycle liquid providing a combined liquid feed ratio in the range of about 1.25 to about 6.0. The operating temperature again alludes to the temperature of the catalyst within the reaction zone, and is in the range of about 400° F. to about 900° F. Since the principal reactions are exothermic in nature, the increasing temperature gradient, experienced as the charge stock traverses the catalyst bed, results in an outlet temperature higher than that at the inlet to the catalyst bed. The maximum catalyst temperature should not exceed 900° F., and it is generally a preferred technique to limit the temperature increase to 100° F. or less.

Although amorphous composites of alumina and silica, containing from about 10.0 to about 90.0% by weight of the latter, are suitable for use in the catalytic composite employed in the present process, a preferred carrier material constitutes a crystalline aluminosilicate, preferably faujasite, of which at least about 90.0% by weight is zeolitic. This carrier material, and a method of preparing the same, have hereinbefore been described.

A specific illustration of this hydrocarbon hydroprocessing technique involves the use of a catalytic composite of about 0.4% by weight of platinum, 0.375% by weight of tin, 0.7% by weight of combined chlorine, and 2% by weight of cobalt, combined with a crystalline aluminosilicate material of which about 90.9% by weight constitutes faujasite. This catalyst is intended for utilization in the conversion of 16,000 Bbl/day of a blend of light gas oils to produce maximum quantities of a heptane-400° F. gasoline boiling range fraction. The charge stock has a gravity of 33.8° API, and has an initial boiling point 369° F., a 50% volumetric distillation temperature of 494° F. and an end boiling point of 655° F. The charge stock is initially subjected to a clean-up operation at maximum catalyst temperature of 750° F., an LHSV of 1.0 with a hydrogen circulation rate of about 5000 scf./Bbl. The pressure imposed upon the catalyst within the reaction zone is about 1,500 psig. Since at least a portion of the blended gas oil charge stock will be converted into lower-boiling hydrocarbon products, the effluent from this clean-up reaction zone is separated to provide a normally liquid, 400° F.-plus charge for the hydrocracking reaction zone containing the hereinabove described catalyst. The pressure imposed upon the second reaction zone is about 1,500 psig., and the hydrogen circulation rate is about 8,000 scf./Bbl. The original quantity of fresh feed to the clean-up reaction zone is about 16,000 Bbl./day; following separation of the first zone effluent to provide the 400° F.-plus change to the second reaction zone, the charge to the second reaction zone is in an amount of about 12,150 Bbl./day, providing an LHSV of 0.85. The temperature at the inlet to the catalyst bed is 665° F., and a conventional hydrogen quench stream is utilized to maintain the maximum reactor outlet temperature at about 700° F. Following separation of the product effluent from the second reaction zone, to concentrate the desired gasoline boiling range fraction, the remaining 400° F.-plus normally liquid material, in an amount of 7,290 Bbl./day, recycled to the inlet of the second reaction zone, thus providing a combined liquid feed ratio thereto of about 1.60. In the following table, there is indicated the product yield and distribution of this process. With respect to normally liquid hydrocarbons, for convenience including butanes, the yields are given in vol. %; with respect to the normally gaseous hydrocarbons, ammonia and hydrogen sulfide, the yields are given in terms of wt. %. With respect to the first reaction zone, the hydrogen consumption is 1.31% by weight of the fresh feed (741 scf./Bbl.), and for the hycdrocracking reaction zone, 1.26% by weight of the fresh feed charge stock, or 713 scf./Bbl.

TABLE

| Hydrocracking Product Yield and Distribution | | | |
| --- | --- | --- | --- |
| Component | Stage I | Stage II | Total |
| Ammonia | 0.01 | — | 0.01 |
| Hydrogen Sulfide | 0.21 | — | 0.21 |
| Methane | 0.12 | 0.02 | 0.14 |
| Ethane | 0.22 | 0.40 | 0.62 |
| Propane | 1.03 | 3.48 | 4.51 |
| Butanes | 3.90 | 14.66 | 18.56 |

TABLE-continued

Hydrocracking Product Yield and Distribution

| Component | Stage I | Stage II | Total |
|---|---|---|---|
| Pentanes | 3.04 | 11.28 | 14.32 |
| Hexanes | 3.00 | 11.21 | 14.21 |
| C$_7$-400° F. | 18.85 | 49.56 | 68.41 |
| 400° F.-plus | 75.92* | — | — |

*Charge to Stage II

With respect to both the butane product and pentane product, the former is indicated as being about 68.0% isobutanes, while the latter constitutes about 93.0% isopentanes. An analysis of the combined pentane/hexane fraction indicates a gravity of 82.6° API, a clear research octane rating of 85.0 and a leaded research octane rating of 99.0; it will be noted that this constitutes an excellent blending component for motor fuel. The desired heptane-400° F. product indicates a gravity of 48.8° API, a clear research octane rating of 72.0 and a leaded research octane rating of 88.0. This gasoline boiling range fraction constitutes about 34.0% by volume paraffins, 36.0% by volume naphthenes and 30.0% by volume aromatic hydrocarbons. It will be recognized that this gasoline boiling range fraction constitutes an excellent charge stock for a catalytic reforming unit to improve the motor fuel characteristics thereof.

The foregoing specification, and particularly the examples, indicates the method by which the present invention is effected, and the benefits afforded through the utilization thereof.

We claim as our invention:

1. A hydrocarbon process which comprises reacting a hydrocarbon with hydrogen at conditions selected to effect chemical consumption of hydrogen, and in contact with a catalytic composite comprising a porous carrier material containing, on an elemental basis, about 0.01 to about 2 wt.% platinum group metal, about 0.5 to about 5 wt.% cobalt, about 0.01 to about 5 wt.% tin and about 0.1 to about 3.5 wt.% halogen, wherein the platinum group metal, cobalt and tin are uniformly dispersed throughout the porous carrier material, wherein substantially all of the platinum group metal is present in the elemental metallic state, wherein substantially all of the tin is present in an oxidation state above that of the elemental metal, and wherein substantially all of the catalytically available cobalt is present in the elemental metallic state or in a state which is reducible to the elemental metallic state under hydrocarbon conversion conditions.

2. The process of claim 1 further characterized in that said conditions include a pressure of from about 400 to about 5000 psig., a liquid hourly space velocity of from about 0.1 to about 10, a hydrogen circulation rate of from about 1000 to about 50,000 scf/bbl and a maximum catalyst temperature of from about 200° F. to about 900° F.

3. The process of claim 1 further characterized in that said carrier material is a crystalline aluminosilicate.

4. The process of claim 1 further characterized in that said carrier material is an amorphous refractory inorganic oxide.

5. A process for hydrogenating a coke-forming hydrocarbon distillate containing di-olefinic and mono-olefinic hydrocarbons, and aromatics, which process comprises reacting said distillate with hydrogen, at a temperature below about 500° F., in contact with a catalytic composite comprising a porous carrier material containing, on an elemental basis, about 0.01 to about 2 wt.% platinum group metal, about 0.5 to about 5 wt.% cobalt, about 0.01 to about 5 wt.% tin and about 0.1 to about 3.5 wt.% halogen, wherein the platinum group metal, cobalt and tin are uniformly dispersed throughout the porous carrier material, wherein substantially all of the platinum group metal is present in the elemental metallic state, wherein substantially all of the tin is present in an oxidation state above that of the elemental metal, and wherein substantially all of the catalytically available cobalt is present in the elemental metallic state or in a state which is reducible to the elemental metallic state under hydrocarbon conversion conditions, and an alkali metal component, and recovering an aromatic/mono-olefinic hydrocarbon concentrate substantially free from conjugated di-olefinic hydrocarbons.

6. A process for hydrocracking a hydrocarbonaceous charge stock into lower molecular weight hydrocarbons, which process comprises reacting said charge stock with hydrogen at hydrocracking conditions, and in contact with a catalytic composite comprising a porous carrier material containing, on an elemental basis, about 0.01 to about 2 wt.% platinum group metal, about 0.5 to about 5 wt.% cobalt, about 0.01 to about 5 wt.% tin and about 0.1 to about 3.5 wt.% halogen, wherein the platinum group metal, cobalt and tin are unformly dispersed throughout the porous carrier material, wherein substantially all of the platinum group metal is present in the elemental metallic state, wherein substantially all of the tin is present in an oxidation state above that of the elemental metal, and wherein substantially all of the catalytically available cobalt is present in the elemental metallic state or in a state which is reducible to the elemental metallic state under hydrocarbon conversion conditions, and separating the resulting reaction zone effluent to recover said lower molecular weight hydrocarbons.

* * * * *